(12) United States Patent
Bartholomew et al.

(10) Patent No.: US 7,867,204 B2
(45) Date of Patent: Jan. 11, 2011

(54) NEEDLELESS ACCESS PORT VALVES

(75) Inventors: Joel Bartholomew, Danielsville, PA (US); Peter W. Peppel, Nazareth, PA (US); Michael J. Janders, Northampton, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 1204 days.

(21) Appl. No.: 11/418,599

(22) Filed: May 4, 2006

(65) Prior Publication Data

US 2007/0260195 A1 Nov. 8, 2007

(51) Int. Cl.
*A61M 5/00* (2006.01)

(52) U.S. Cl. ............... 604/249; 604/167.03; 604/244; 604/323; 604/350; 251/337

(58) Field of Classification Search ............ 604/167.03, 604/244–247, 249, 256, 323, 335, 350, 533, 604/537, 905, 213; 251/149.6, 149.4, 149.1, 251/337
See application file for complete search history.

(56) References Cited

U.S. PATENT DOCUMENTS

| | | | |
|---|---|---|---|
| 3,570,484 A * | 3/1971 | Steer et al. | 604/249 |
| 3,806,086 A * | 4/1974 | Cloyd | 251/149.7 |
| 4,197,848 A | 4/1980 | Garrett et al. | |
| 4,506,691 A * | 3/1985 | Tseo | 137/1 |
| 4,535,819 A | 8/1985 | Atkinson et al. | |
| 4,765,588 A | 8/1988 | Atkinson | |
| 4,819,684 A * | 4/1989 | Zaugg et al. | 137/112 |
| 4,883,467 A | 11/1989 | Franetzki et al. | |
| 4,934,655 A | 6/1990 | Blenkush et al. | |
| 4,953,594 A | 9/1990 | Von Berg | |
| 5,006,114 A | 4/1991 | Rogers et al. | |
| 5,049,128 A | 9/1991 | Duquette | |
| 5,065,783 A | 11/1991 | Ogle, II | |
| 5,085,645 A | 2/1992 | Purdy et al. | |
| 5,104,389 A | 4/1992 | Deem et al. | |
| 5,108,380 A | 4/1992 | Herlitze et al. | |
| 5,147,333 A | 9/1992 | Raines | |
| 5,163,922 A | 11/1992 | McElveen, Jr. et al. | |
| 5,190,523 A | 3/1993 | Lindmayer | |
| 5,203,775 A | 4/1993 | Frank et al. | |
| 5,230,706 A | 7/1993 | Duquette | |
| 5,242,393 A | 9/1993 | Brimhall et al. | |
| 5,242,423 A | 9/1993 | Goodsir et al. | |
| 5,251,873 A | 10/1993 | Atkinson et al. | |
| 5,269,771 A * | 12/1993 | Thomas et al. | 604/539 |
| 5,281,206 A | 1/1994 | Lopez | |
| 5,289,849 A | 3/1994 | Paradis | |
| 5,322,516 A | 6/1994 | Brugger | |
| 5,330,450 A | 7/1994 | Lopez | |

(Continued)

*Primary Examiner*—Nicholas D Lucchesi
*Assistant Examiner*—Quynh-Nhu H Vu
(74) *Attorney, Agent, or Firm*—Klein, O'Neill & Singh, LLP (57) ABSTRACT

Needleless access port valves are generally discussed herein with particular discussions extended to needleless access port valves having a stretchable or flexible band. In accordance with aspects of the present invention, the band is held in between a flange section of an inlet connector assembly and a shoulder section of the valve body. A plunger integrally formed with the band is movable inside a nozzle to control fluid flow through the inlet of the valve. When the plunger is urged by a medical implement to open the valve inlet, the band flexes to accommodate the moving plunger.

20 Claims, 3 Drawing Sheets

U.S. PATENT DOCUMENTS

| | | | |
|---|---|---|---|
| 5,336,174 A | 8/1994 | Daoud et al. | |
| 5,344,414 A | 9/1994 | Lopez et al. | |
| 5,353,837 A | 10/1994 | Faust | |
| 5,360,413 A * | 11/1994 | Leason et al. | 604/249 |
| 5,380,306 A | 1/1995 | Brinon | |
| 5,390,898 A | 2/1995 | Smedley et al. | |
| 5,395,348 A | 3/1995 | Ryan | |
| 5,401,245 A | 3/1995 | Haining | |
| 5,409,463 A | 4/1995 | Thomas et al. | |
| 5,251,873 A | 5/1995 | Atkinson et al. | |
| 5,423,791 A | 6/1995 | Bartlett | |
| 5,425,465 A | 6/1995 | Healy | |
| 5,439,451 A | 8/1995 | Collinson et al. | |
| 5,441,487 A | 8/1995 | Vedder | |
| 5,462,255 A | 10/1995 | Rosen et al. | |
| 5,466,219 A | 11/1995 | Lynn et al. | |
| 5,509,433 A | 4/1996 | Paradis | |
| 5,509,912 A | 4/1996 | Vaillancourt et al. | |
| 5,533,983 A * | 7/1996 | Haining | 604/249 |
| 5,535,771 A | 7/1996 | Purdy et al. | |
| 5,535,785 A | 7/1996 | Werge et al. | |
| 5,540,661 A | 7/1996 | Tomisaka et al. | |
| 5,549,577 A | 8/1996 | Siegel et al. | |
| 5,569,235 A | 10/1996 | Ross et al. | |
| 5,573,516 A | 11/1996 | Tyner | |
| 5,584,808 A | 12/1996 | Healy | |
| 5,616,129 A | 4/1997 | Mayer | |
| 5,620,434 A | 4/1997 | Brony | |
| 5,624,414 A | 4/1997 | Boettger | |
| 5,645,538 A | 7/1997 | Richmond | |
| 5,674,206 A | 10/1997 | Allton et al. | |
| 5,676,346 A | 10/1997 | Leinsing | |
| 5,685,866 A | 11/1997 | Lopez | |
| 5,690,612 A | 11/1997 | Lopez et al. | |
| 5,694,686 A | 12/1997 | Lopez | |
| 5,695,466 A | 12/1997 | Lopez et al. | |
| 5,699,821 A | 12/1997 | Paradis | |
| 5,700,248 A | 12/1997 | Lopez | |
| 5,730,418 A | 3/1998 | Feith et al. | |
| 5,738,663 A | 4/1998 | Lopez | |
| 5,743,894 A | 4/1998 | Swisher | |
| RE35,841 E | 7/1998 | Frank et al. | |
| 5,776,113 A | 7/1998 | Daugherty et al. | |
| 5,782,816 A | 7/1998 | Werschmidt et al. | |
| 5,785,693 A * | 7/1998 | Haining | 604/249 |
| 5,788,215 A | 8/1998 | Ryan | |
| 5,806,551 A | 9/1998 | Meloul et al. | |
| 5,806,831 A | 9/1998 | Paradis | |
| 5,810,768 A | 9/1998 | Lopez | |
| 5,810,792 A | 9/1998 | Fangrow, Jr. et al. | |
| 5,810,793 A | 9/1998 | Boettger | |
| 5,839,715 A | 11/1998 | Leinsing | |
| 5,848,994 A | 12/1998 | Richmond | |
| 5,873,862 A | 2/1999 | Lopez | |
| 5,879,327 A | 3/1999 | Moreau DeFarges et al. | |
| 5,901,942 A | 5/1999 | Lopez | |
| 5,921,264 A | 7/1999 | Paradis | |
| 5,921,419 A | 7/1999 | Niedospial, Jr. et al. | |
| 5,928,204 A | 7/1999 | Lopez | |
| 5,957,898 A | 9/1999 | Jepson et al. | |
| 5,967,490 A | 10/1999 | Pike | |
| 5,971,950 A | 10/1999 | Lopez et al. | |
| 6,019,748 A | 2/2000 | Lopez | |
| 6,029,946 A | 2/2000 | Doyle | |
| 6,036,171 A | 3/2000 | Weinheimer et al. | |
| 6,039,302 A | 3/2000 | Cote, Sr. et al. | |
| 6,040,366 A | 3/2000 | Burkus, II et al. | |
| 6,045,534 A | 4/2000 | Jacobsen et al. | |
| 6,063,062 A | 5/2000 | Paradis | |
| 6,068,011 A | 5/2000 | Paradis | |
| 6,083,194 A | 7/2000 | Lopez | |
| 6,106,502 A | 8/2000 | Richmond | |
| 6,113,068 A | 9/2000 | Ryan | |
| 6,117,114 A | 9/2000 | Paradis | |
| 6,127,320 A | 10/2000 | van Ooij et al. | |
| 6,132,403 A | 10/2000 | Lopez | |
| 6,132,404 A | 10/2000 | Lopez | |
| 6,142,446 A | 11/2000 | Leinsing | |
| 6,152,900 A | 11/2000 | Mayer | |
| 6,168,137 B1 | 1/2001 | Paradis | |
| 6,170,800 B1 | 1/2001 | Meloul et al. | |
| 6,171,287 B1 | 1/2001 | Lynn et al. | |
| 6,189,859 B1 | 2/2001 | Rohrbough et al. | |
| 6,228,069 B1 | 5/2001 | Barth et al. | |
| 6,245,048 B1 | 6/2001 | Fangrow, Jr. et al. | |
| 6,245,056 B1 | 6/2001 | Walker et al. | |
| 6,261,268 B1 | 7/2001 | Mayer | |
| 6,261,282 B1 | 7/2001 | Jepson et al. | |
| 6,273,869 B1 | 8/2001 | Vaillancourt | |
| 6,290,206 B1 * | 9/2001 | Doyle | 251/149.1 |
| 6,290,688 B1 | 9/2001 | Lopez et al. | |
| 6,299,131 B1 | 10/2001 | Ryan | |
| 6,299,132 B1 | 10/2001 | Weinheimer et al. | |
| 6,325,782 B1 | 12/2001 | Lopez | |
| 6,344,033 B1 | 2/2002 | Jepson et al. | |
| 6,364,869 B1 | 4/2002 | Bonaldo | |
| 6,428,520 B1 | 8/2002 | Lopez et al. | |
| 6,482,188 B1 * | 11/2002 | Rogers et al. | 604/249 |
| 6,491,668 B1 | 12/2002 | Paradis | |
| 6,541,802 B2 | 4/2003 | Doyle | |
| RE38,145 E | 6/2003 | Lynn | |
| 6,572,591 B2 | 6/2003 | Mayer | |
| 6,572,592 B1 | 6/2003 | Lopez | |
| 6,585,229 B2 | 7/2003 | Cote, Sr. et al. | |
| 6,599,273 B1 | 7/2003 | Lopez | |
| 6,616,627 B2 | 9/2003 | Willis et al. | |
| 6,626,418 B2 | 9/2003 | Kiehne | |
| 6,635,044 B2 | 10/2003 | Lopez | |
| 6,641,561 B1 | 11/2003 | Hill et al. | |
| 6,645,170 B2 | 11/2003 | Landau | |
| 6,669,673 B2 | 12/2003 | Lopez | |
| 6,669,681 B2 | 12/2003 | Jepson et al. | |
| 6,682,509 B2 | 1/2004 | Lopez | |
| 6,695,817 B1 | 2/2004 | Fangrow, Jr. | |
| 6,706,022 B1 | 3/2004 | Leinsing et al. | |
| 6,755,391 B2 | 6/2004 | Newton et al. | |
| 6,758,833 B2 | 7/2004 | Lopez | |
| 6,802,490 B2 | 10/2004 | Leinsing et al. | |
| 6,840,501 B2 | 1/2005 | Doyle | |
| 6,855,138 B2 | 2/2005 | Tsai | |
| 6,869,426 B2 | 3/2005 | Ganem | |
| 6,871,838 B2 | 3/2005 | Raines et al. | |
| 6,991,215 B2 * | 1/2006 | Kiehne | 251/149.6 |
| 7,635,357 B2 * | 12/2009 | Mayer | 604/256 |
| 2003/0032940 A1 | 2/2003 | Doyle | |
| 2003/0060779 A1 | 3/2003 | Richmond | |
| 2003/0136932 A1 | 7/2003 | Doyle | |

\* cited by examiner

NEEDLELESS ACCESS PORT VALVES

Needleless access port valves are generally discussed herein with particular discussions extended to needleless access port valves comprising a stretchable or flexible band.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless access port valve assembly comprising a plunger assembly comprising a band adapted to flex when urged by a medical implement; the band, which comprises a length and a cross-sectional circumference of smaller dimension than the length, is compressed along two opposed surfaces between an inlet connector assembly comprising a port and a valve body comprising a port; said band integrally formed with a plunger and comprising an arcuate shaped structure extending from the plunger, the band being compressed between a seat on the valve body and a seat on the inlet connector assembly.

The present invention may also be practiced by providing a needleless access port valve assembly comprising a plunger assembly comprising an axially extending plunger and an integrally formed band disposed in between an inlet connector assembly comprising an inlet port and a valve body comprising an outlet port; said inlet connector assembly and said valve body defining a groove and at least a portion of said band is disposed in said groove and being compressed thereby; wherein said band comprises a first length when said plunger is in a first position and a second length, which is longer than the first length, when said plunger is in a second position.

In yet another aspect of the present invention, there is provided a needleless access port valve assembly comprising an inlet connector assembly comprising an inlet port, a plunger assembly means, and a valve body comprising an outlet port, said plunger assembly means comprising an integrally formed plunger and spring means compressed in between a groove defined by a flange on the inlet connector assembly and a shoulder on the valve body; wherein the spring means flexes in response to a force applied on the plunger and is less flexed when said force is removed from said plunger.

In yet another aspect of the present invention, there is provided a cavity in the plunger section of the plunger assembly and a rigid plug disposed in the cavity.

In still yet another aspect of the present invention, there is provided a retaining channel in the valve body for retaining the band. The retaining channel have a graded base for accommodating the travel of the band and/or the plunger.

Other aspects and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

DETAILED DESCRIPTION

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Figure 1:
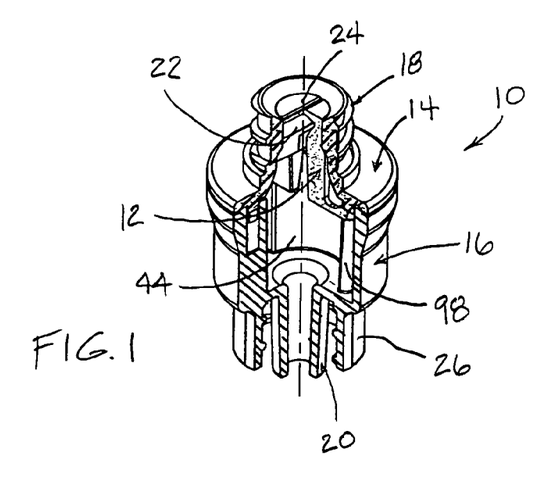
FIG. 1 is a semi-schematic cut-away perspective view of a needleless access port valve provided in accordance with aspects of the present invention; which shows the plunger assembly in a first or closed position.

Turning now to FIG. 1, a semi-schematic cut-away perspective view of a valve assembly provided in accordance with aspects of the present invention is shown, which is generally designated 10. In one exemplary embodiment, the valve assembly comprises a plunger assembly 12, an inlet connector assembly 14, and a valve body 16. As further discussed below, the plunger assembly 12 is wedged in between the inlet connector assembly 14 and the valve body 16 and is configured to control fluid flow through the valve inlet 18 and the valve outlet 20. More particularly, when the plunger 22 of the plunger assembly 14 is in the first or closed position as shown, fluid flow is obstructed and no flow is permitted through the opening 24 of the valve inlet 18. In one exemplary embodiment, the valve inlet 18 comprises a threaded female luer for threaded engagement with a first medical implement, such as a syringe, and the outlet 20 comprises a threaded male luer comprising a threaded collar 26 for threaded engagement with a second medical implement, such as an IV catheter set.

Figure 2:
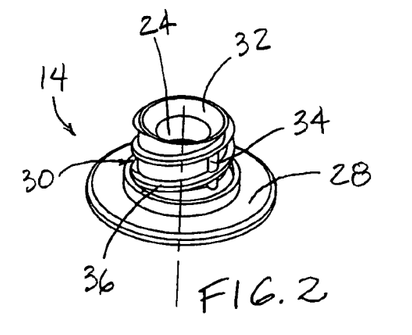
FIG. 2 is a semi-schematic perspective view of an inlet connector assembly provided in accordance with aspects of the present invention.

Referring now to FIG. 2, a semi-schematic perspective view of the inlet connector assembly 14 of FIG. 1 is shown. In one exemplary embodiment, the inlet connector assembly 14 comprises a flange 28 and a nozzle 30, which cooperates with the plunger 22 to form the valve inlet 18. The nozzle 30 comprises a tapered inlet 32 for facilitating insertion of a medical implement (not shown), such as a syringe, a male luer fitting, a tubing, etc., by directing the male end of the medical implement towards the opening 22. In a preferred embodiment, two or more interference ribs 34 are incorporated with the external threads 36 for greater interference fit between the nozzle 30 and a threaded collar of a medical implement.

Figure 3:
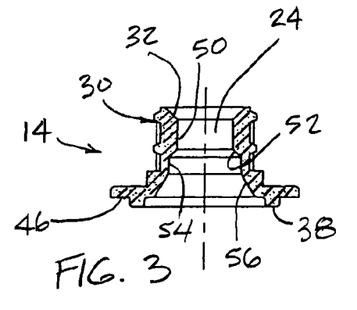
FIG. 3 is a semi-schematic cross-sectional side view of the inlet connector assembly of FIG. 2.

FIG. 3 is a semi-schematic cross-sectional side view of the inlet connector assembly 14 of FIG. 2. In one exemplary embodiment, a short stub or collar 38 extends axially in the opposite direction from the nozzle 30. The short stub 38 is configured to compress the resilient coils or bands 40 (FIG. 4) on the plunger assembly 12 against the retaining channels 42 (FIGS. 7-8) on the valve body 16 to retain the plunger assembly 12 in an operative position inside the interior cavity 42 of the valve 10. A flange seat 46 is positioned adjacent the short stub 38. The flange seat 46 is configured to abut against the end collar 48 (FIG. 8) on the valve body 16 and the seam defined therebetween glued or welded.

In one exemplary embodiment, the interior surface of the nozzle 30 comprises an entry section 50 comprising a standard luer taper, a first tapered section 52, a mid section 54, and a second tapered section 56. In a preferred embodiment, the first tapered section 52 functions as a shoulder for a tapered abutment against a corresponding tapered section on the plunger 22 to form a seal at the valve inlet 18. Alternatively or in addition thereto, the entry section 50 and the mid section 54 of the nozzle 30 are configured to abut against corresponding surfaces on the plunger 22 to provide additional sealing points for the inlet 18. In yet alternative embodiment, only the entry section 50 and the first tapered section 52 are configured to abut against corresponding surfaces on the plunger 22 to form a sealing point for the inlet 18. In still yet another alternative embodiment, only the first tapered section 52 is configured to abut against a corresponding surface on the plunger 22 to form sealing points for the inlet 18. In one exemplary embodiment, the second tapered section 56 functions as a return guide to channel or funnel the plunger 22 from an open or a second position back towards a first or closed position. A plurality of internal ribs defining a plurality of flow channels may be incorporated in the interior cavity of the nozzle for facilitating fluid flow. The inlet connector assembly 14 may be made from a rigid plastic material. Exemplary rigid plastic materials include polycarbonate, polystyrene, polypropylene, or their equivalence.

Figure 4:
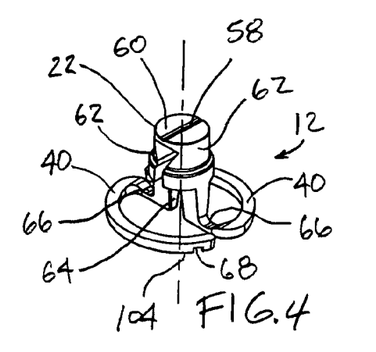
FIG. 4 is a semi-schematic perspective view of a plunger assembly provided in accordance with aspects of the present invention; which comprises a stretch band.

FIG. 4 is a semi-schematic perspective view of a plunger assembly 12 provided in accordance with aspects of the present invention. In one exemplary embodiment, the plunger assembly comprises a trough or channel 58 on the top surface 60 of the plunger 22. The trough 58 defines a vertical plane, which separates the plunger assembly 12 into two symmetrical halves. The trough 58 is also configured to provide flow space for fluid flow flowing either from a medical implement through the valve 10 or from the valve towards the medical implement. Each half comprises a plunger half 62, and a resilient coil or band 40. The band 40 comprises a cross-sectional circumference comprising a dimension and a length. The cross-sectional dimension being less than the length. A main channel 64 is incorporated in between the two plunger halves 62 and coincident with the plane defined by the trough 58. The main channel 64 has a height in the direction of the vertical plane and varying widths in the direction perpendicular to the vertical plane. The widths vary along the selected configuration of the main channel 64, See, e.g., FIG. 5, which may differ in configuration from the shaped main channel shown.

When the plunger assembly 12 is positioned in the interior cavity 44 of the valve 10 and the top surface 60 of the plunger 22 pushed distally away from the opening 22 by a medical implement, the two resilient coils 40 flex and the main channel 64 widens. In other words, if the main channel 64 comprises a width X at a particular point along the main channel, then the width increases to X+Y when the plunger 22 is engaged by a medical implement and is pushed distally in the direction of the outlet port 20. When the medical implement is subsequently removed, the plunger assembly 12 rebounds to its more relaxed state and the width returns to its first width X.

In one exemplary embodiment, the coils 40 are connected to the two plunger halves 62 by a bridge 66, which has varying thicknesses for facilitating bending. The coils 40 each comprises an arcuate shape and has a generally uniform thickness along the length of the coil with varying thicknesses contemplated. A recessed channel 68 defining a hook is located at an end of each coil 40. Each hook 68 is configured to engage a lever or anchor 70 located in the channel 42 of the valve body 16 to keep the coil from dislodging from the channel 42 and/or rotating within the channel. In one exemplary embodiment, the plunger assembly 12 is made from a thermoplastic elastomer. An elastomeric plastic of a thermoplastic elastomer (TPE) type such as the copolyamide (COPA) family of thermoplastic elastomers may be used. In one exemplary embodiment, the COPA is copolyamide thermoplastic elastomer having a commercial trade name PEBAX®. However, other TPEs may also be used to make the inlet connector assembly 12, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. In a more preferred embodiment, the thermoplastic elastomer is SANTOPRENE® material from Advance Elastomer Systems.

Figure 5:
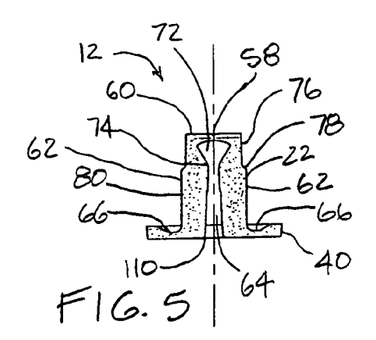
FIG. 5 is a semi-schematic cross-sectional side view of the plunger assembly of FIG. 4.

FIG. 5 is a semi-schematic cross-sectional side view of the plunger assembly 12 of FIG. 4. In one exemplary embodiment, an upper channel section 72 of the main channel 64 comprises a fan shape configuration. The upper plunger section 60 adjacent the upper channel section 72 is more narrowed at the center of the fan shape configuration and gradually thickens as it extends radially outwardly. At about the base 74 of the fan shape configuration and extending axially towards the coils or bands 40, the main channel 64 comprises a gradually increasing cone shape configuration. However, other shaped configuration may be incorporated for the main channel 64 provided sufficient girth or material, flexible and resilient properties are provided for the plunger 22 and the coil springs to ensure rebounding or recoiling when pushed by a medical implement.

Externally, the plunger 22 comprises an upper section 76 comprising a luer taper for a standard luer taper contact with the entry section 50 of the nozzle 30 (FIG. 3). A shoulder 78 comprising an enlarged neck section distal of the upper section 76 is incorporated to abut against the first tapered section 52 on the nozzle 30 in a tapered contact. A lower section 80 comprising a luer taper is positioned distal of the shoulder 78 and functions as a plunger base.

Figure 6:
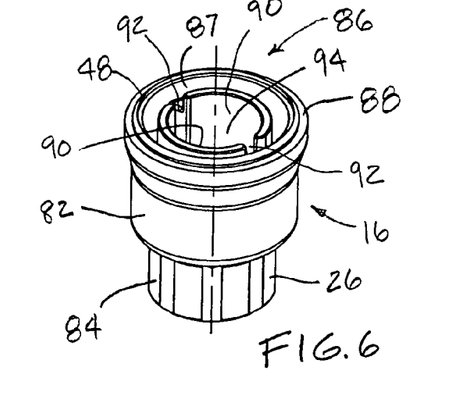
FIG. 6 is a semi-schematic perspective view of a valve body provided in accordance with aspects of the present invention.

FIG. 6 is a semi-schematic perspective view of the valve body 16 of FIG. 1. The valve body 16 comprises a central body section 82 and an outlet section 84 comprising the valve outlet 20 and the threaded collar 26. At the opening end 86 of the central body section 82, the end collar 48 is positioned slightly above a plane defined by the end edge or end shoulder 88 of the central body section 82. As previously discussed, the flange seat 46 of the inlet connector assembly 14 is configured to abut the end collar 48 and the seam defined therebetween sealed via adhesive or welding.

Internally, an interior wall surface 87 of the central body section 82 and two channel walls 90 separated by two seams 92 define two retaining channels 42. The two retaining channels 42 are adapted to receive the two resilient coils 40 on the plunger assembly 12 while the two seams 92 are adapted to receive the two bridges 66. A central cavity 94 bounded by the two channel walls 90 is adapted to accommodate movement of the plunger 22 when the same is urged by a medical implement.

Figure 7:
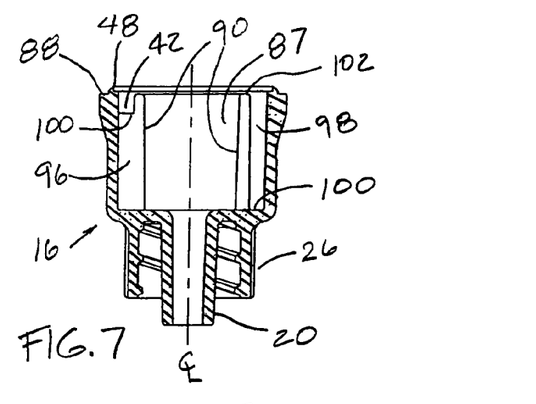
FIG. 7 is a semi-schematic cross-sectional side view of the valve body of FIG. 7.
Figure 8:
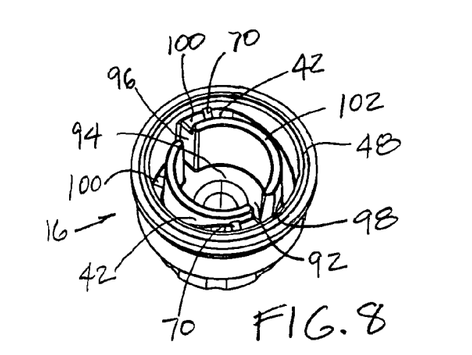
FIG. 8 is a semi-schematic partial perspective view of the valve body of FIG. 6 from a different viewing plane.

Turning now to FIG. 7 in addition to FIG. 8, each retaining channel 42 comprises an end wall 96 and an end channel opening 98. Each retaining channel 42 comprises a channel base or channel seat 100. Assuming the valve body 16 comprises a centerline $L$ (FIG. 7), the channel seat 100 is preferably angled, i.e., has a grade, as it extends from the end comprising the end wall 96 towards the end comprising the end channel opening 98. Thus, the height measured from the channel base 100 to the end edge 102 of the channel wall 90 at or near the end wall 96 is less than the height measured from the channel base 100 to the end edge 102 of the channel wall 90 at or near the end channel opening 98. In one exemplary embodiment, the two retaining channels 42 have unidirectional angled channel bases or seats 100. In other words, both channel bases or seats 100 are angled in a clockwise direction.

However, a counter-clockwise taper may be incorporated without deviating from the spirit and scope of the present invention. Alternatively, instead of incorporating angled seats, a drop off comprising a cliff or vertical wall may be incorporated. The change in elevation in each of the channel bases 100 is configured to provide space for accommodating the resilient coil 40 when the same flexes, as further discussed below.

Figure 9:
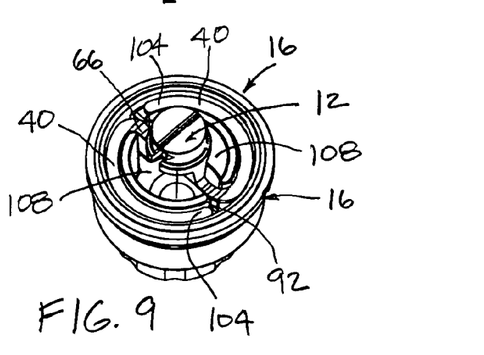
FIG. 9 is a semi-schematic partial perspective view of the plunger assembly of FIG. 4 mounted inside the valve body of FIG. 8.

Turning now to FIG. 9 in addition to FIGS. 4 and 8, the plunger assembly 12 is positioned in the valve body 16 by placing the two resilient coils 40 in the two retaining channels 42 while aligning the two bridges 66 with the two seams 92. The recessed channels 68 on the resilient coils 40 are positioned over the two bumps 70 on the channel seats 100. In this configuration, only the ends 104 (FIG. 9) of the two resilient coils 40 rest against the channel seats 100 while the remaining sections of the two resilient coils 40 are spaced apart from the channel seats 100. The spatial relationship between the two allows for movement of the coils 40.

Figure 10:
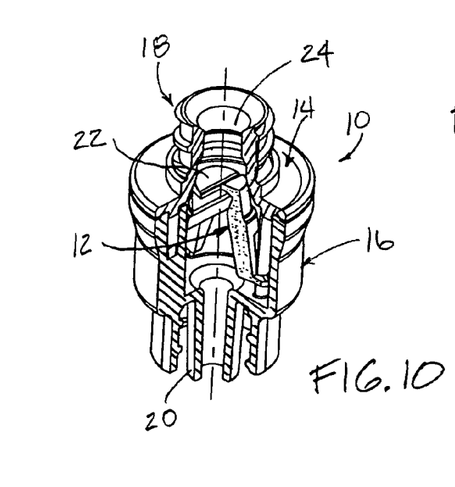
FIG. 10 is a semi-schematic cut-away perspective view of the valve of FIG. 1 with the plunger assembly in a second or used position.
Figure 11:
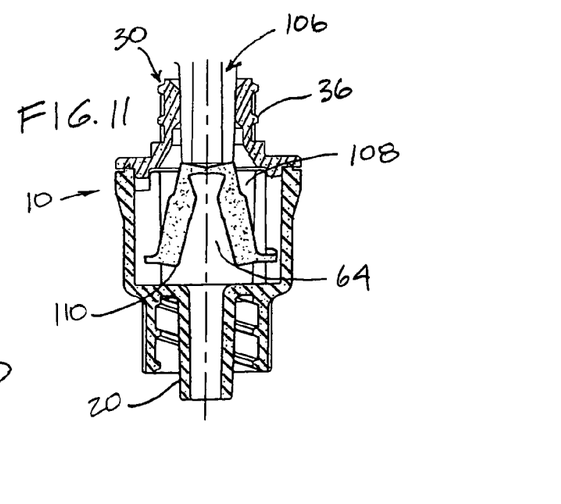
FIG. 11 is a semi-schematic cross-sectional side view of the valve 10 with the plunger assembly moved to the second position by a medical implement.

FIGS. 10 and 11 show the valve assembly 10 in a second or used position. FIG. 10 shows the plunger 22 urged axially distally away from the inlet opening 24 and the valve inlet 18 in fluid communication with the valve outlet 20. As is readily apparent to a person of ordinary skill in the art, the medical implement that normally urges the plunger 22 into the second position is not shown for clarity. FIG. 11 is a cross-sectional side view of the valve 10 in a used position with a male tip of a medical implement 106 partially shown.

In the used position, fluid flow through the valve 10 flows through the flow space 108 located between the channel walls 90 and the plunger 22. A fluid flow space 110 is also provided between the end tip of the medical implement 106 and the top surface 60 of the plunger 22. Alternatively or in addition thereto, protrusions or bumps may be incorporated on the top surface 60 of the plunger 22 to provide fluid flow space for fluid flow flowing either from the medical implement through the valve 10 or towards the medical implement. As previously discussed, flow channels may be incorporated on the interior wall surface of the nozzle 30 for fluid flow.

Comparing the plunger 22 in the normal or first position (e.g., FIG. 5) versus the same in a used position (e.g., FIG. 11), it is clear that the gap of the main channel 64 at the base 110 of the plunger 22, as well as other places along the main channel 64, widens or increases when the plunger 22 moves from a first position to a second or used position. As previously discussed, this widening is caused, at least in part, by the resilient coils 40 flexing in response to the pressure applied by the medical implement on the plunger 22, which then flexes the two coils 40, which are attached to the plunger 22 at the two bridges 66 and pull apart the plunger. When the medical implement 106 is subsequently removed and the load or force lifted off of the plunger 22, the flexible and resilient coils 40 rebound to their less flexed position, which in turn move the plunger 22 from the second position to the first position to seal the opening 24 of the valve 10. In one preferred embodiment, a positive flush is created whereby residual fluid located internally of the valve is pushed out the outlet upon removal of the medical implement 106 from the inlet. This flushing action is provided by ensuring an internal fluid space decrease upon removal of the medical implement, which creates a increase in internal pressure to thereby create a positive flush. However, the valve may be a neutral valve, i.e., no flush, or a negative flush valve without deviating from the spirit and scope of the present invention.

Figure 12:
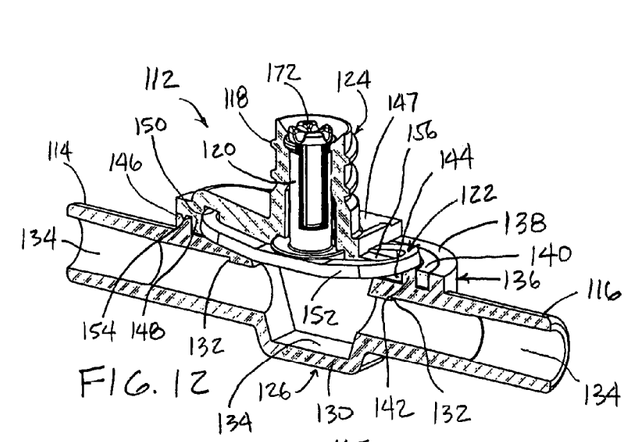
FIG. 12 is a semi-schematic cut-away perspective view of an alternative needleless access port valve provided in accordance with aspects of the present invention; which shows the plunger assembly in a first or closed position.

Turning now to FIG. 12, a semi-schematic cut-away perspective view of an alternative needleless injection port valve provided in accordance with aspects of the present invention is shown, which is generally designated 112. The valve 112 is commonly referred to as a Y-site valve and incorporates a first port 114, a second port 116, and a third port 118. As is readily apparent to a person of ordinary skill in the art, the name and number designations for the three ports can vary without deviating from the spirit and scope of the present invention. Whereas the first and second ports 114, 116 are always in fluid communication with one another, the third port or valve inlet port 118 is only in fluid communication with the first and second ports 114, 116 when the plunger 120 moves from a first position, shown in FIG. 12, to a second position, shown in FIG. 15.

Similar to the first valve embodiment 10, the present valve 112 comprises a plunger assembly 122, an inlet connector assembly 124, and a valve body 126. The valve is assembled by placing the plunger assembly 122 on the valve seat of the valve body 126, placing the inlet connector assembly 124 over the plunger assembly, and gluing or welding the seam 128 between the valve body and the inlet connector assembly, as further discussed below. In a preferred embodiment, the seam is welded, using for example, laser welding or high frequency welding.

In one exemplary embodiment, the valve body 126 comprises a base 130 having the two ports 114, 116 extending outwardly therefrom at a 180° angle from one another with other angles contemplated. The two ports 114, 116 incorporate standard tubing dimensions for mating engagement with IV tubes or tubing. Preferably, a ledge or shoulder 132 is incorporated in the lumen 134 of each port to delimit the extent of insertion of the tubing inside the two ports. In one exemplary embodiment, the base 130 comprises an interior surface 134 positioned at an elevation below the elevation of the first and second ports 114, 116. This relative configuration is configured to accommodate the travel of the plunger 120, and the band attached to the plunger, when the same is pushed by a medical implement, as further discussed below.

A shoulder section 136 comprising a first seat 138, a groove 140, a second seat 142, and a platform 142 is incorporated to support the plunger assembly 122 and to mate with the inlet connector assembly 124. The inlet connector assembly 124 incorporates a corresponding first seat 146 on the flange 147 for abutting contact with the first seat 138 on the shoulder section 136, a tongue 148 for mating with the groove 140 in a tongue-and-groove configuration, and a groove 150 for receiving a flexible coil spring or band 152 on the plunger assembly 122. Preferably, the various dimensions of the various components are such that a slight compression is applied on the coil or band 152 when the components are fully assembled. In one exemplary embodiment, a protrusion 154 is incorporated on the first seat 146 of the flange section for added compression against the second seat 142. In a preferred embodiment, a pair of integrally formed beams 156 are incorporated on the underside of the flange 147 of the inlet connector assembly 124. The beams 156 are configured to shore or support the coil spring 152 and prevent the same from displacing from the second seat 142 from the shoulder section 136 of the valve body. In one exemplary embodiment, the beams 156 each comprises an end face (not shown) and the end face either contacts or is positioned slightly space apart from a side edge of the second seat 142 to prevent the coil spring 152 from dislodging from the second seat. In one exemplary embodiment, the spring 152 is held by the inlet connector assembly 124 and the valve body 126 only along the ends of the band thus allowing the lengthwise direction of the oblong shape band to more freely deflect or move.

Figure 13:
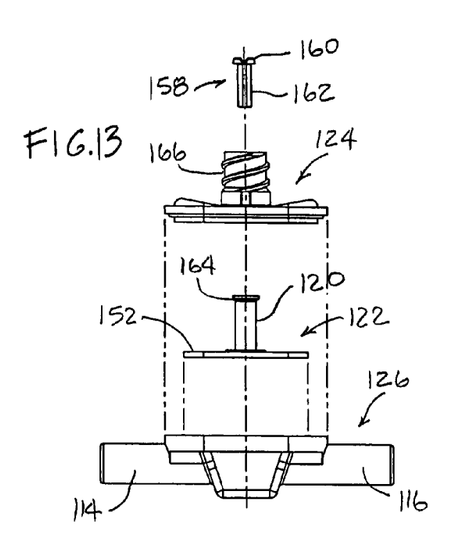
FIG. 13 is a semi-schematic exploded side view of the valve of FIG. 12, which shows various valve components.
Figure 14:
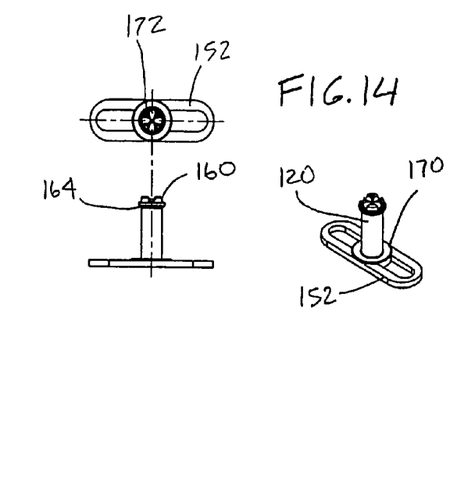
FIG. 14 is a multi-view of the plunger assembly of FIGS. 12 and 13.

FIG. 13 is a semi-schematic exploded side view of the valve 112 of FIG. 12. In one exemplary embodiment, the plunger assembly 122 is made from a thermoplastic elastomer comprising flexible and resilient properties. Exemplary thermoplastics include SANTOPRENE®. The material allows the resilient coil to flex when the plunger 122 is pushed by a medical implement and return to its less flexed configuration when the medical implement is removed. As further discussed below, while the plunger 120 may be made entirely from a semi-rigid thermoplastic material, in a preferred embodiment, the plunger 120 has a hollow central cavity and a plug 158 made from a rigid thermoplastic material positioned within the hollow central cavity. With reference to FIG. 14, the plug 158 comprises a head 160 and a stem 162. The stem 162 is configured to reside internally of the central cavity of the plunger 120 while the head 160 remains external of the plunger. Preferably, the plunger 120 grips the stem 162 by sizing the dimension of the stem to slightly stretch the plunger.

A circumferential band, lip, or seal 164 is incorporated at the proximal end of the plunger 120. The band 164 comprises a cross-sectional first dimension, the lumen 165 (FIG. 15) of the inlet nozzle 166 comprises a cross-sectional second dimension, and wherein the first dimension is larger than the second dimension. Thus, when the plug 158 is seated within the plunger 120, the lip 164 is compressed by the interior surface of the nozzle 166 and the stem 162. The compressed lip 164 functions as an O-ring to provide a seal for the lumen of the third port 118. Alternatively or in addition thereto, a shoulder may be incorporated on the plunger 120 for sealing engagement with a corresponding shoulder 168 inside the interior cavity of the nozzle 166 of the inlet connector assembly 124.

Referring again to FIG. 14, the coil spring 152 comprises a generally oval or oblong configuration. The coil spring 152 is integrally formed with the plunger 120 and in a preferred embodiment is connected to a plunger base 170, which has a cross-sectional dimension that is larger than the cross-sectional dimension of the plunger 120. Instead of viewing the coil spring 152 as an oblong shaped spring, the spring may be viewed as comprising two separate U-shape springs or bands extending from the plunger 120. In an alternative embodiment, the plunger 120 may incorporate a main channel similar to the plunger incorporated in the valve 10 of FIG. 1. Also shown in FIG. 14 are ridges or protrusions 172 located on the top surface of the head 160 of the rigid plug 158. In a preferred embodiment, four ridges 172 defining four flow channels therebetween are incorporated. The flow channels provide flow space for fluid flow flowing either from a medical implement or towards the medical implement.

Figure 15:
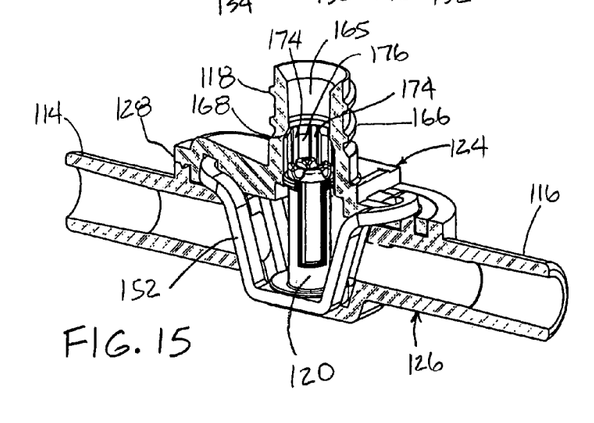
FIG. 15 is a semi-schematic cut-away perspective view of the alternative needleless access port valve of FIG. 12; which shows the plunger assembly in a second or used position

FIG. 15 shows the plunger 120 being displaced from its first position to its second position by a medical implement, which is not shown for clarity. In the position shown, fluid communication is open between all three ports 114, 116, 118. Fluid flow flowing either from or towards the third port 118 flows around the plunger 120 through a plurality of channels 174 formed between internal ribs 176 on the interior surface of the nozzle 166. The internal ribs 176 and channels 174 are formed below the perimeter opening of the nozzle 166. Thus, the plunger 120 must be displaced downwardly a sufficient amount from the opening before fluid flow is permitted via the plurality of channels 174. The base 130 of the valve body 126, therefore, should be sufficiently deep to adequately accommodate the travel of the plunger 120 and the band 152. In a preferred embodiment, four or more channels are incorporated in the interior cavity of the nozzle 166. More preferably, six channels 174 are incorporated.

Although limited embodiments of the needleless access valve assemblies and their components have been specifically described and illustrated herein, many modifications and variations will be apparent to those skilled in the art. For example, the various valves may incorporate luer-slips rather than luer threads, the material selected could be opaque or semi-opaque, different colors may be used, the dimensions can vary, etc. Furthermore, it is understood and contemplated that features specifically discussed for one valve embodiment may be adopted for inclusion with another valve embodiment, provided the functions are compatible. For example, certain curvatures and contours incorporated in one valve may be incorporated in another valve for aesthetic appeal and improved functionality, such as for improved gripping purposes. Accordingly, it is to be understood that the valve assemblies and their components constructed according to principles of this invention may be embodied other than as specifically described herein. The invention is also defined in the following claims.

What is claimed is:

1. A needleless access port valve assembly comprising a plunger assembly comprising a continuous band adapted to flex and stretch when urged by a medical implement; the band, which comprises a length and a cross-sectional circumference of smaller dimension than the length, is compressed only along two opposed surfaces between an inlet connector assembly comprising a port and a valve body comprising a port; said band integrally formed with a plunger comprising a base; the band being compressed between a seat on the valve body and a seat on the inlet connector assembly and comprising an arcuate shaped structure having two hollow cavities located between the plunger and the band such that part of the base is exposed at the cavities.

2. The needleless access port valve of claim 1, wherein the cross-sectional circumference comprises a plurality of sides and edges.

3. The needleless access port valve of claim 1, wherein the plunger further comprises an upper surface and a channel originating at the base and extending towards the upper surface.

4. The needleless access port valve of claim 1, wherein the valve body comprises an exterior wall surface and an interior channel wall defining a channel therebetween.

5. The needleless access port valve of claim 1, wherein the band comprises a perimeter with a constant thickness throughout.

6. The needleless access port valve of claim 5, wherein the band has an oblong shape.

7. The needleless access port valve of claim 1, further comprising a flow channel located on an upper surface of the plunger.

8. The needleless access port valve of claim 1, wherein the valve body comprises a groove for mating with the inlet connector assembly.

9. A needleless access port valve assembly comprising a plunger assembly comprising an axially extending plunger and an integrally formed band having a perimeter with a constant thickness throughout, the band being disposed in between an inlet connector assembly comprising an inlet port and a valve body comprising an outlet port; said inlet connector assembly and said valve body defining a groove and only a portion of said band perimeter with the constant thickness throughout is disposed in said groove and being compressed thereby; wherein said band and said band perimeter comprise a first length when said plunger is in a first position and a second length, which is longer than the first length, when said plunger is in a second position.

10. The needleless access port valve assembly of claim 9, wherein the band comprises a cross-sectional circumference of smaller dimension than the first length.

11. The needleless access port valve assembly of claim 9, wherein the plunger comprises a channel originating from proximate the band and extending upwardly towards an upper surface.

12. The needleless access port valve assembly of claim 10, wherein the cross-sectional circumference comprises a plurality of sides and edges.

13. The needleless access port valve assembly of claim 9, wherein the plunger assembly comprises at least one hollow cavity located between the plunger and the band perimeter.

14. The needleless access port valve of claim 9, wherein the band has an oblong shape.

15. The needleless access port valve assembly of claim 9, wherein the valve body further comprises a second groove for mating with the inlet connector assembly.

16. A needleless access port valve assembly comprising an inlet connector assembly comprising an inlet port, a plunger assembly means for regulating fluid flow, and a valve body comprising an outlet port, said plunger assembly means comprising an integrally formed plunger comprising a base, spring means for stretching and unstretching having a perimeter, and at least one hollow cavity disposed between the plunger and the spring means, the at least one hollow cavity extending to the base of the plunger, the spring means and perimeter being compressed in between a groove defined by a flange on the inlet connector assembly and a shoulder on the valve body; wherein the spring means and perimeter flex in response to a force applied on the plunger and are less flexed when said force is removed from said plunger.

17. The needleless access port valve assembly of claim 16, wherein the valve body further comprises a second groove for mating with the inlet connector assembly.

18. The needleless access port valve assembly of claim 16, wherein the flange on the inlet connector assembly comprises a pair of integrally formed beams for further supporting the spring means.

19. The needleless access port valve assembly of claim 16, wherein the perimeter has a constant thickness throughout.

20. The needleless access port valve assembly of claim 19, wherein the spring means has an oblong shape.

* * * * *

UNITED STATES PATENT AND TRADEMARK OFFICE
CERTIFICATE OF CORRECTION

| | | |
|---|---|---|
| PATENT NO. | : 7,867,204 B2 | Page 1 of 1 |
| APPLICATION NO. | : 11/418599 | |
| DATED | : January 11, 2011 | |
| INVENTOR(S) | : Joel Bartholomew et al. | |

It is certified that error appears in the above-identified patent and that said Letters Patent is hereby corrected as shown below:

In column 2, line 67, after "position" insert -- . --.

In column 10, line 24, in Claim 14, after "valve" insert -- assembly --.

Signed and Sealed this

Twenty-third Day of August, 2011

David J. Kappos
*Director of the United States Patent and Trademark Office*